United States Patent
Sakoda et al.

(10) Patent No.: US 9,364,453 B2
(45) Date of Patent: Jun. 14, 2016

(54) METHOD OF TREATING POSTURAL REFLEX ABNORMALITY CAUSED BY PARKINSON'S DISEASE

(75) Inventors: Saburo Sakoda, Hyogo (JP); Kei Fukada, Osaka (JP)

(73) Assignee: Lundbeck NA Ltd., Wilmington, DE (US)

( * ) Notice: Subject to any disclaimer, the term of this patent is extended or adjusted under 35 U.S.C. 154(b) by 0 days.

(21) Appl. No.: 14/117,506

(22) PCT Filed: Jun. 14, 2012

(86) PCT No.: PCT/US2012/037770
§ 371 (c)(1),
(2), (4) Date: Nov. 13, 2013

(87) PCT Pub. No.: WO2012/158612
PCT Pub. Date: Nov. 22, 2012

(65) Prior Publication Data
US 2014/0378546 A1    Dec. 25, 2014

(30) Foreign Application Priority Data

May 17, 2011    (JP) .................. 2011-110179

(51) Int. Cl.
| | |
|---|---|
| *A61K 31/198* | (2006.01) |
| *A61K 31/122* | (2006.01) |
| *A61K 31/275* | (2006.01) |
| *A61K 31/165* | (2006.01) |
| *A61K 45/06* | (2006.01) |

(52) U.S. Cl.
CPC ............. *A61K 31/198* (2013.01); *A61K 31/122* (2013.01); *A61K 31/165* (2013.01); *A61K 31/275* (2013.01); *A61K 45/06* (2013.01); *A61K 2300/00* (2013.01)

(58) Field of Classification Search
CPC .................................................... A61K 31/198
See application file for complete search history.

(56) References Cited

U.S. PATENT DOCUMENTS

| | | | |
|---|---|---|---|
| 3,920,728 A | 11/1975 | Hegedüs et al. | |
| 4,246,428 A | 1/1981 | Ohashi et al. | |
| 4,319,046 A | 3/1982 | Vacek | |
| 4,330,558 A | 5/1982 | Suzuki et al. | |
| 4,421,767 A | 12/1983 | Palfreyman et al. | |
| 4,480,109 A | 10/1984 | Ohashi et al. | |
| 4,497,826 A | 2/1985 | Narabayashi et al. | |
| 4,529,603 A | 7/1985 | Mori et al. | |
| 4,562,263 A | 12/1985 | Ohashi et al. | |
| 4,647,587 A | 3/1987 | Katsube et al. | |
| 4,690,949 A | 9/1987 | Yoshida et al. | |
| 4,699,879 A | 10/1987 | Umezawa et al. | |
| 4,963,590 A | 10/1990 | Bäckström et al. | |
| 5,015,564 A | 5/1991 | Chari | |
| 5,240,930 A | 8/1993 | Al-Damluji | |
| 5,266,596 A | 11/1993 | Yokokawa et al. | |
| 5,616,618 A | 4/1997 | Takagi | |
| 5,656,669 A | 8/1997 | Nishino | |
| 5,739,387 A | 4/1998 | Oda et al. | |
| 5,864,041 A | 1/1999 | Oda et al. | |
| 6,033,993 A | 3/2000 | Love, Jr. et al. | |
| 6,132,714 A | 10/2000 | Tang et al. | |
| 6,150,412 A | 11/2000 | Pystynen et al. | |
| 6,387,936 B1 | 5/2002 | Blanchard-Bregeon et al. | |
| 6,512,136 B1 | 1/2003 | Benes et al. | |
| 6,610,324 B2 | 8/2003 | Stoll | |
| 6,610,690 B2 | 8/2003 | Wong et al. | |
| 6,653,325 B2 | 11/2003 | Svensson | |
| 6,703,424 B2 | 3/2004 | Levin et al. | |
| 6,746,688 B1 | 6/2004 | Kushnir et al. | |
| 6,929,801 B2 | 8/2005 | Klose et al. | |
| 6,992,110 B2 | 1/2006 | Kranzler et al. | |
| 2001/0007856 A1 | 7/2001 | Nishino | |
| 2001/0047032 A1 | 11/2001 | Castillo et al. | |
| 2002/0177593 A1 | 11/2002 | Ishihara et al. | |
| 2003/0181509 A1 | 9/2003 | Hinz | |
| 2004/0013620 A1 | 1/2004 | Klose et al. | |
| 2004/0152760 A1 | 8/2004 | Castillo et al. | |

(Continued)

FOREIGN PATENT DOCUMENTS

| | | |
|---|---|---|
| EP | 0237 929 | 9/1987 |
| GB | 2 200 109 A | 7/1988 |

(Continued)

OTHER PUBLICATIONS

Han, et al. AAPS Pharmsci. (2000), vol. 2 (1) article 6, pp. 1-11.*
Ettmayer, et al. J. Med. Chem. (2004), vol. 47 (10), pp. 2393-2404.*
Testa, et al. Biochem. Pharm. (2004), vol. 68, pp. 2097-2106.*
http://web.archive.org/web/20050831044729/http://courses.washington.edu/chat543/evans/sfp/catechol.html, "Catecholamines as Neurotransmitters/Hormones," University of Washington—School of Medicine, Cardiovascular & Autonomic Pharmacology module, Aug. 31, 2005, pp. 1-7.
Agmo et al., "A Rat Model Of Distractibility: Effects of Drugs Modifying Dopaminergic, Noradrenergic and GABA Ergic Neurotransmission," *Journal of Neural Transmission*, 1997, pp. 11-29, vol. 104, No. 1. http://www.springerlink.com/content/n66254211q511485/.
Ammirati et al., "Effects of Intravenous Etilefrine in Neurocardiogenic Syncope Induced by Head-up Tilt Testing," *The American Journal of Cardiology*, 2000, pp. 472-474, vol. 86.

(Continued)

*Primary Examiner* — Noble Jarrell
*Assistant Examiner* — John S Kenyon
(74) *Attorney, Agent, or Firm* — Womble Carlyle Sandridge & Rice, LLP

(57) ABSTRACT

The present disclosure relates to a more effective therapeutic agent capable of improving and treating the axial symptoms (particularly freezing of gait symptom) of patients with Parkinson's disease. Such symptoms in patients with Parkinson's disease can be improved and treated by using L-threo-3,4-dihydroxy-phenylserine (DOPS) and a COMT inhibitor in combination together, optionally with an L-DOPA preparation as well. As a result, the axial symptoms difficult to improve with conventional L-DOPA preparations can be treated, and a therapeutic agent and a treatment method are provided for the axial symptoms of patients with Parkinson's disease, particularly those suffering from the disease at a moderate level or higher.

18 Claims, 1 Drawing Sheet

(56) References Cited

U.S. PATENT DOCUMENTS

| | | | |
|---|---|---|---|
| 2005/0043408 | A1 | 2/2005 | Yeboah et al. |
| 2005/0096387 | A1 | 5/2005 | Verheijen et al. |
| 2005/0233010 | A1 | 10/2005 | Satow |
| 2006/0035976 | A1 | 2/2006 | Peroutka |
| 2007/0004639 | A1 | 1/2007 | Kane et al. |
| 2008/0221170 | A1 | 9/2008 | Roberts et al. |
| 2008/0227830 | A1 | 9/2008 | Roberts et al. |
| 2009/0023705 | A1 | 1/2009 | Roberts et al. |
| 2009/0074861 | A1 | 3/2009 | Ochiai et al. |
| 2010/0286124 | A1 | 11/2010 | Gant et al. |
| 2013/0197090 | A1* | 8/2013 | Hewitt et al. ............. 514/567 |

FOREIGN PATENT DOCUMENTS

| | | |
|---|---|---|
| WO | WO 01/32170 | 5/2001 |
| WO | WO 2004/032844 A2 | 4/2004 |
| WO | WO 2004/100929 A1 | 11/2004 |
| WO | WO 2005/085178 A | 9/2005 |
| WO | WO2006/123678 | 11/2006 |
| WO | WO 2007/112014 A2 | 10/2007 |
| WO | WO 2008/003028 A2 | 1/2008 |
| WO | WO 2010/054286 | 5/2010 |
| WO | WO 2011/001976 | 1/2011 |
| WO | WO 2011/085216 | 7/2011 |

OTHER PUBLICATIONS

Bennett, et al., "A Peripheral Mononeuropathy in Rat That Produces Disorders of Pain Sensation Like Those Seen in Man," *Pain*, 1988, pp. 87-107, vol. 33, No. 1.

Bradley et al., "Orthostatic Hypotension," *American Family Physician*, 2003, pp. 2393-2398, vol. 68, No. 12.

Brannan et al., "L-threo-DOPS Increases Extracellular Norepinephrine Levels in The Brain: An In Vivo Study," *Neurology*, 1990, pp. 1134-5, 40(7).

Brzostowska et al., "Phenylcarbamates of (-)-Eseroline, (-)-N1-Noreseroline and (-)-Physovenol: Selective Inhibitors of Acetyl and, or Butyrylcholinesterase", *Medical Chemistry Research*, 1992, pp. 238-246, vol. 2, No. 4.

Calkins et al., "Relationship Between Chronic Fatigue Syndrome and Neurally Mediated Hypotension," *Cardiology in Review.* (1998), pp. 125-134, vol. 6, No. 3.

Cryan et al., "Norepinephrine-Deficient Mice Lack Responses to Antidepressant Drugs, Including Selective Serotonin Reuptake Inhibitors," *PNAS*, 2004, pp. 8186-8191, vol. 101, No. 21. www.pnas.org/cgi/doi/10.1073/pnas.0401080101.

Dableh et al., "Antidepressant-like Effects of Neurokinin Receptor Antagonists in the Forced Swim Test in the Rat," *European Journal of Pharmacology*, 2005, pp. 99-105, vol. 507.

Dadabhoy et al., Therapy Insight: Fibromyalgia—a Different Type of Pain Needing a Different Type of Treatment, *Nature Clinical Practice. Rheumatology*, 2006, pp. 364-372, vol. 2.

Dhir et al., "Etiect of Addition of Yohimbine (Alpha-2-Receptor Antagonist) to the Antidepressant Activity of Fluoxetine or Venlafaxine in the Mouse Forced Swim Test," *Pharmacology*, 2007, 239-243, vol. 80.

Edvinsson et al., "Effect of Exogenous Noradrenaline on Local Cerebral Blood Flow After Osmotic Opening of the Blood-Brain Barrier in the Rat," *J. Physiol*, 1978, pp. 149-156, vol. 274.

Flippen-Anderson et al., Thiaphysovenol Phenylcarbamates: X-ray Structures of Biologically Active and Inactive Anticholinesterase Agents, *Heterocycles*, 1993, pp. 79-86, vol. 36, No. 1.

Garcia-Borreguero et al., "Parkinson's Disease and Sleep," *Sleep Medicine Reviews*, 2003, 7(2), pp. 115-129.

Gilden, "Midodrine in Neurogenic Orthostatic Hypotension. A New Treatment," *International Angiology*, 1998, vol. 17(3), pp. 125-131.

Goldstein, "L-Dihydroxyphenylserine (L-DOPS): A Norepinephrine Prodrug," *Cardiovascular Drug Reviews*, 2006, pp. 189-203, vol. 24, No. 3-4.

Goswami et al., "Characterization of a Flavoprotein Iodotyrosine Deiodinase from Bovine Thyroid," *The Journal of Biological Chemistry*, 1979, pp. 12326-12330, vol. 254. No. 24.

Goto et al., "Depression in Multiple System Atrophy: A case Report," *Psychiatry and Clinical Neurosciences*, 2000, pp. 507-511, vol. 54.

Greig et al. "Phenserine and Ring C Hetero-Analogues: Drug Candidates for the Treatment of Alzheimer's Disease." *Medicinal Research Reviews*. (1995) vol. 15, No. 1, 3-31.

He et al. "Thiaphysovenine and Carbamate Analogues: A New Class of Potent Inhibitors of Cholinesterases." *Medical Chemistry Research*. (1992) vol. 2, 229-237.

Iida et al., "Effects of L-Threo-3,4-Dihydroxyphenylserine on Orthostatic Hypotension in Hemodialysis Patients," *American Journal of Nephrology*, 2002, pp. 338-346, vol. 22, No. 4, Basel.

Joo, et al., "Cerebral Perfusion Abnormality in Narcolepsy with Cateaplexy," *NeuroImage*, 2005, pp. 410-416, vol. 28, No. 2.

Kato et al., "Reversal of the Reserpine-Induced Ptosis by L-Threo-3,4-Dihydroxy-Phenylserine (L-Threo-DOPS), A (-)-Norepinephrine Precursor, and Its Potentiation By Imipramine or Nialamide," *Naunyn-Schiniedeberg's Archies of Pharmacology*, 1986, pp. 243-246, vol. 332, No. 3, Berlin.

Kato et al., "Studies on the Activity of L-Threo-3,4-Dihydroxyphenylserine (L-DOPS) As a Catecholamine Precursor in the Brain, Comparison With Taat of L-DOPA," *Biochemical Pharmacology*, 1987, pp. 3051-3057, vol. 36, No. 18, Great Britain.

Kaufmann et al., "Midodrine in Neurally Mediated Syncope: A Double-Blind Randomized, Crossover Study," *Annals of Neurology*, 2002, vol. 52, pp. 342-345.

Kaufmann et al., "Norepinehrine Precursor Therapy in Neurogenic Orthostatic Hypotension," *Circulation*, 2003, pp. 724-28, 108.

Kawabata et al., "The Noradrenaline Precursor L-Threo-3,4-Dihydroxyphenylserine Exhibits Antinociceptive Activity Via Central Alpha-Adrenoceptors In The Mouse," *Br J. Pharmacol*. 1994, pp. 503-508, vol. 111, No. 2, Japan.

Kim et al., "Methylphenidate Increased Regional Cerebral Blood Flow in Subjects with Attention Deficit/Hyperactivity Disorder," *Yonsei Medical Journal*, 2001, pp. 19-29, vol. 42, No. 1.

Komiya et al., "The Effectivity of L-threo-3, 4-dihydroxyphenylserine (L-threo-DOPS) to the Hypersomnia and the Subcortal Dementia Caused by Bilateral Medial Thalamic and Midbrains Infarcts" *Clin. Neurol.*, 1988, pp. 268-271, vol. 28, No. 3.

Lahiri et al. "Cholinesterase Inhibitors, β-Amyloid Precursor Protein and Amyloid β-Peptides in Alzheimer's Disease." *Acta Neurologica Scandinavia*. (Dec. 2000) vol. 102 (s176), 60-67.

Lamberti et al., "Antidepressant-like Effects of Endogenous Histamine and of Two Histamine $H_1$ Receptor Agonists in the Mouse Forced Swim Test," *British Journal of Pharmacology*, 1998, pp. 1331-1336, vol. 123.

Lawson, "Tricyclic Antidepressants and Fibromyalgia: What is the Mechanism of Action?," *Expert Opinion on Investigational Drugs*, 2002, pp. 1437-1445, vol. 12.

Lee et al., "Regional Cerebral Blood Flow in Children With Attention Deficit Hyperactivity Disorder: Comparison Before and After Methylphenidate Treatment," *Human Brain Mapping*, 2005, pp. 157-164, vol. 24, No. 3.

Lou et al., "Focal Cerebral Hypoperfusion in Children With Dysphasia and/or Attention Deficit Disorder," *Archives of Neurology*, 1984, pp. 825-829, vol. 41, No. 8.

Martignoni et al., "Cardiovascular Dysautonomia as a Cause of Falls in Parkinson's Disease," *Parkinsonism and Related Disorders*, 2006, pp. 195-204, vol. 12.

Mease et al., "Fibromyalgia: Should the Treatment Paradigm be Monotherapy or Combination Pharmacotherapy?," *Current Pain and Headache Reports*, 2008, pp. 399-405, vol. 12.

Moldes et al. "The Actions of Dihydroxyphenylalanine and Dihydroxyphenylserine On The Sleep-Wakefulness Cycle Of The Rat After Peripheral Decarboxylase Inhibition," *Br J Pharmacol*, 1975, pp. 101-106, vol. 54, No. 1.

Mori et al., "Effects of L-Erythro-3, 4-Dihydroxyphenylserine on Sleep-Wakefulness Patterns and Concentrations of Brain Catecholamines and Serotonin in Rats," *Jpn J Psychiatry Neurol*, 1987, pp. 301-10, vol. 41, No. 2.

Morissette et al., "High-Throughput Crystallization: Polymorphs, Salts, Co-Crystals and Solvates of Pharmaceutical Solids," *Advanced Drug Delivery Reviews*, 2004, pp. 275-300, vol. 56.

(56) References Cited

OTHER PUBLICATIONS

Myllylä et al., Effect of Entacapone, a COMT Inhibitor, on the Pharmacokinetics of Levodopa and on Cardiovascular Responses in Patients with Parkinson's Disease, 1993, *Euro J. Clin Pharmacol.*, 1993, pp. 419-423, vol. 45.

NIH—National Institute of Neurological Disorders and Stroke: Information sheet on orthostatic hypotension (2007). Accessed online Aug. 30, 2010 at http://www.ninds.nih.gov/disorders/orthostatic_hypotension/orthostatic_hypotension.htm?css=print.

Noto et al., "Effects of L-Threo- And Erythro-3,4-Dihydroxyphenylserine On Learning Performance And Concentrations of Brain Noradrenaline And Its Metabolites in Rats," *Pharmacol Biochem Behav.*, 1992, pp. 215-221, vol. 43, No. 1.

Pei et al. "Total Synthesis of Racemic and Optically Active Compounds Related to Physostigimine and Ring-C Heteroanalogues from 3[-2'-(Dimethylamino0ethyl]-2,3-dihydro-5-methoxy-1, 3-dimentyl-1H-indol-2-ol." *Helvetica Chimica ACTA.* (1994), pp. 1412-1422, vol. 77.

Rowe et al., "Is Neurally Mediated Hypotension an Unrecognised Cause of Chronic Fatigue?" *The Lancet*, 1995, pp. 623-624, vol. 345.

Russell, "Advances in Fibromyalgia: Possible Role for Central Neurochemicals," *Am J Med Sci.*, 1998, pp. 377-384, vol. 315, No. 6.

Porsolt et al., "Behavioural Despair in Mice: A primary Screening Test for antidepressants," *Arch. Int. Pharmacodyn*, 1977, pp. 327-336, vol. 229.

Schroeder et al., Norepinephrine Transporter Inhibition Prevents Tilt-Induced Pre-Syncope, *Journal of the American College of Cardiology*, 2006, pp. 516-522, vol. 48, No. 3.

Schondorf, "Acetylcholinesterase Inhibition in the Treatment of Hypotension," *Journal of Neurology Neurosurgery and Psychiatry*, 2003, pp. 1187, vol. 74, No. 9, www.jnnp.bmjjournals.com_,.

Scott, et al., "Randomized Comparison of Atenolol and Fludrocortisone Acetate in the Treatment of Pediatric Neurally Mediated Syncope," *The American Journal of Cardiology*, 1995, pp. 400-402, vol. 76.

Singer et al. "Pyridostigmine Treatment Trial in Neurogenic Orthostatic Hypotension", 2006, *Archives of Neurology*. vol. 63, No. 4, pp. 513-518. www.archneur.ama-assn.org.

Takagi et al., "Analgesic Effect of L-Threo-3,4-Dihydroxyphenylserine (L-DOPS) In Patients With Chronic Pain," *Eur Neuropsychopharmacol.*, 1996, pp. 43-47, vol. 6, No. 1, Japan.

Tanaka et al., "The Effects of the Noradrenaline Precursor, L-Threo-3,4-Dihydroxy-Phenylserine, in Children With Orthostatic Intolerance," *Clinical Autonomic Research*, 1996, pp. 189-193, vol. 6.

Toda et al., "Parkinson Disease Patient with Fibromyalgia: A Case Report" *Parkinsonism and Related Disorders*, 2007, pp. 312-312, vol. 13.

Tulen et al., "Sleeping With and Without Norepinephrine: Effects Of Metoclopramide and D,L-Threo-3,4- Dihydroxyphenylserine On Sleep In Dopamine Beta-Hydroxylase Deficiency," *Sleep*, 1991, pp. 32-38, vol. 14, No. 1. The Netherlands.

Verhagen-Kamerbeek, et al. "Attenuation of Haloperidol-Induced Catalepsy by Noradrenaline and L-Threo-DOPS," *Journal of Neural Transmission. Parkinson's Disease and Dementia Section*, 1993, pp. 17-26, vol. 6. No. 1, Austria.

Vippagunta et al., "Crystalline Solids," *Advanced Drug Delivery Reviews*, 2001, pp. 3-26, vol. 48.

Webster's Online Dictionary. Definition of ischemia. Accessed online Aug. 30, 2010 at http://www.websters-dictionary-online.org/definitions/ischemia?ex-partner-pub-0939450753529744%3Av0qd01-tdlq&cof=FORID%3A9&ie=UTF-8&q=ischemia&sa=Search.

Yamamoto et al., "Pyridostigmine in Autonomic Failure: Can We Treat Postural Hypotension and Bladder Dysfunction With One Drug?" *Clinical Autonomic Research*, 2006, pp. 296-298, vol. 16, No. 4.

Yoshida etal., "Inhibitory Effects Of L-Threo-DOPS On Electroshock Seizure In Mice," *Brain and Nerve*, 1989, pp. 567-573, vol. 41, No. 6, Japan.

Yu et al. al. "Novel Phenserine-Based-Selective Inhibitors of Butyrylcholinesterase for Alzheimer's Disease." Reprinted with permission from *J. Med. Chem.*, May 20, 1999, 42, 1855-1861.

Yu et al. "Total Syntheses and Anticholinesterase Activities of (3aS)-N (8)-Norphysostigmine, (3aS)-N (8)-Norphenserine, Their Antipodal Isomers, and Other N (8)-Substituted Analogues." *J. Med. Chem.* (1997) vol. 40, 2895-2901.

Yunus, "Fibromyalgia and Overlapping Disorders: The Unifying Concept of Central Sensitivity Syndromes," *Semin. Arthritis Rheum.*, 2007, pp. 339-356, vol. 36.

Zern et al., "Effect of Increased Pancreatic Islet Norepinephrine, Dopamine and Serotonin Concentration On Insulin Secretion In the Golden Hamster," *Diabetologia*, 1980, pp. 341-346, vol. 18, No. 4, Berlin.

www.merck.com , "Orthostatic Hypotension and Syncope," *The Merck Manual of Diagnosis and Therapy*, 1996, Sec. 16, Chapter 200.

Gupta et al., "Neurogenic Orthostatic Hypotension: Chasing "the fall"," *Postgraduate Medical Journal*, 2008, pp. 6-14, vol. 84, No. 987.

Kaufmann, "L-dihydroxyphenylserine (Droxidopa): A New Therapy for Neurogenic Orthostatic Hypotension," *Clinical Autonomic Research*, 2008, pp. 19-24, vol. 18, No. 1.

Mathias et al., "L-threo-dihydroxyphenylserine (L-threo-DOPS; droxidopa) in the Management of Neurogenic Orthostatic Hypotension: A Multi-National, Multi-Center, Dose-Ranging Study in Multiple System Atrophy and Pure Autonomic Failure," *Clinical Autonomic Research, Rapid Communications*, 2001, pp. 235-242, vol. 11, No. 4.

Wood el al., "Incidence and Prediction of Falls in Parkinson's Disease: A Prospective Multidisciplinary Study," *Journal of Neurology Neurosurgery and Psychiatry*, 2002, pp. 721-725. vol. 72, No. 6.

Bartholini et al., "The Stereoisomers of 3,4-Dihydroxyphenyl-Serine as Precursors of Norepinephrine," *The Journal of Pharmacology and Experimental Therapeutics*, 1975, vol. 193, No. 2, pp. 523-532.

Chang et al., "Review of Excipients and pH's for Parenteral Products Used in the United States," *PDA J. Pharm Sci and Tech*, 1980, vol. 34, pp. 452-462.

Ettmayer et al., "Lessons Learned from Marketed and Investigational Prodrugs," *Journal of Medicinal Chemistry*, 2004, vol. 47, No. 10, pp. 2393-2404.

Han, "Targeted Prodrug Design to Optimized Drug Delivery," *AAPS Pharmsci*, 2000, vol. 2, No. 1, pp. 1-11. www.pharmsci.org.

Mannisto et al., "Catechol-O-methyltransferase (COMT): Biochemistry, Molecular Biology, Pharmacology, and Clinical Efficacy of the New Selective COMT Inhibitors," *Pharmacological Reviews*, vol. 51, No. 4, pp. 593-628. (c) 2010.

The Merck Manual, "Orthostatic Hypotension and Syncope," Sec. 16, Ch. 200, Downloaded Mar. 14, 2006. www.merck.com/mrkshared/mmanual/section16/chaper200/200a.jsp.

Narabayashi et al., "L-Threo-3,4-Dihydroxyphenylserine Treatment for Akinesia and Freezing of Parkinsonism," *Proc. Japan Acad.*, 1981, vol. 57, Ser. B, No. 9, pp. 351-354.

Narabayashi et al., "Therapeutic Effects of L-DOPS in Parkinson's Disease," *Clin. Eval.*, 1987, vol. 15, pp. 423-457.

Remington's Pharmaceutical Sciences, 18th ed., Mack Publishing Company, Eaton, Pa., 1990.

Testa, "Prodrug Research: Futile or Fertile?" *Biochemical Pharmacology*, 2004, vol. 68, pp. 2097-2106.

\* cited by examiner evaluation of freezing of gait

VAS (Visual Analogue Scale)

start of test 0. 2. 4 weeks complete absence 0　　　　　　　　　　　　　　　100　presence of
of freezing of　　├─────────────────────┤　　freezing of
gait　　　　　　　　　　　　　　　　　　　　　　　　　gait, highly
　　　　　　　　　　　　　　　　　　　　　　　　　　inconvenient in
　　　　　　　　　　　　　　　　　　　　　　　　　　daily life month, day, year name of test subject

METHOD OF TREATING POSTURAL REFLEX ABNORMALITY CAUSED BY PARKINSON'S DISEASE

TECHNICAL FIELD

The present invention relates to a therapeutic agent for treating an axial symptom (postural reflex abnormality) of Parkinson's disease, particularly freezing of gait, by using L-threo-3,4-dihydroxy-phenylserine (hereinafter to be abbreviated as DOPS) and a catechol-O-methyltransferase (hereinafter to be abbreviated as COMT) inhibitor.

BACKGROUND

Parkinson's (PA) disease is a neurodegenerative disease showing motor dysfunction as a cardinal symptom. It was first described in 1817 by Doctor James Parkinson, and frequently develops in elderly people. It is a highly universal disease developed with a prevalence today of about 100 in 100,000 people. First, pathomorphological studies of PA disease revealed degeneration and falling off of nerve cells in the nigra-striatum system, and neurobiochemical studies in the latter half of the 1950s revealed that the neurotransmitter of the nerves in the nigra-striatum system is dopamine (hereinafter DA), and severe deficiency of DA was found in PA disease. As a result, a concept has been established that PA disease is a striatal dopamine deficiency syndrome caused by degeneration of DA nerves in the nigra-striatum system.

The above concept was further supported since effectiveness of a DA supplementation therapy with L-dihydroxy-phenylalanine (L-DOPA), which is a DA precursor amino acid, was shown. Elucidative studies of PA disease progressed thereafter, and it is now recognized that PA disease also accompanies denaturation and hypofunction of norepinephrine (hereinafter NE) in the nerve system, though the main lesion is denaturation and hypofunction of the DA nerve system, since denaturation of pons locus-coeruleus, which is a NE nerve, and decrease of DA β-hydroxylase (hereinafter DBH), which is a NE biosynthetic enzyme, are also observed.

Symptoms associated with PA disease are principally divided into symptoms of four limbs (segmental symptoms) and truncal symptoms (axial symptoms). The segmental symptoms are classified into the symptoms of tremor and rigidity, and the axial symptoms are classified into the symptoms of freezing of gait, gait disturbance, abnormal postural sway and so on. The former syndrome of segmental symptoms is attributed to dysfunction of the DA nerve system, since L-DOPA therapy is effective for these symptoms. However, the latter syndrome of axial symptoms, particularly freezing of gait, includes an L-DOPA therapy responsive type and non-responsive type, where the non-responsive type may be ascribed to wide neurodegeneration other than of dopamine neurons.

Based on the above-mentioned main onset mechanism of PA diseases, a previous drug therapy (i.e., use of a DA nerve system activator) has been tried. To be precise, since DA itself cannot cross the blood brain barrier (hereinafter BBB), DA administered peripherally cannot replenish deficient DA in the brain.

On the other hand, since the physiological precursor amino acid, L-DOPA, can penetrate into the brain and is converted there to DA by decarboxylation by aromatic amino acid decarboxylase (hereinafter AADC), it can replenish intracerebral DA deficiency in PA disease (which is the principle of L-DOPA therapy).

Thus, L-DOPA therapy introduced in the 1970s as a treatment method of PA disease still remains the main therapy for PA disease, and a combination drug with peripheral decarboxylase inhibitor (hereinafter DCI) is prevalent at present.

The combination drug with DCI inhibits formation of DA due to decarboxylation in the periphery, which suppresses side effects caused by peripheral DA, such as nausea, vomiting, hypotension and so on, as well as suppresses peripheral L-DOPA inactivation. Therefore, a greater amount of L-DOPA can be transferred into the brain, and the same dose of L-DOPA can enhance the effect and prolong duration of effectiveness, or the same effect can be provided by the administration of a smaller amount. The effect of the latter case can be regarded an economizing effect and DCI providing such effect is sometimes called an economizer.

In addition, as a therapeutic agent for PA disease, a variety of DA nerve system activators have been developed besides L-DOPA preparations. That is, various DA receptor stimulants, DA release enhancers, and L-DOPA activators have been put into practice. These DA neuron activators are used instead of L-DOPA preparations or in combination therewith. Moreover, various anticholinergic agents having an antitremor action have long been used for the treatment of PA disease. Recent new medicaments include monoamine oxidase-type B (hereinafter MAO-B) inhibitors and catechol-O-methyl group transferase inhibitors (hereinafter COMT inhibitor). These drugs are classified as economizers since they enhance administration efficiency by inhibiting an enzyme reaction that inactivates L-DOPA and generates DA. Entacapone, which is a COMT inhibitor recently introduced into the market, was approved for an indication of improving on the decrease of efficacy duration due to a long-term administration in the L-DOPA therapy and diurnal variation (known as "wearing-off phenomenon") where a drug suddenly becomes ineffective.

Based on the secondary onset mechanism of the PA disease, a therapeutic agent for PA disease by a NE nerve system activator has also been tried. Among them, DOPS (general name, Droxidopa) has a unique position.

While DOPS is a nonphysiological amino acid, it is an NE precursor amino acid which is decarboxylated by aromatic amino acid decarboxylase (AADC) and converted to physiological NE. That is, it is assumed that aromatic amino acid DOPS penetrates into the brain, is converted to NE within the brain, replenishes intracerebral NE, and contributes to the treatment of PA disease.

On the other hand, L-DOPA therapy does not provide a significant effect on axial symptoms such as freezing of gait and the like in PA disease. Therefore, Narabayashi et al. (Proc. Japan Acad., 57, Ser. B, No. 9, 351-354(1981)) postulated that these axial symptoms might be due to dysfunction of the NE nerve system. To activate the NE nerve system, he tried administration of racemic DOPS to patients with PA disease with the "freezing of gait symptom", and clinically observed its effect for the first time.

In Japan, the effect was continuously studied by using DOPS in an optically active form, and DOPS was finally approved in 1989 based on the clinical trial results significantly superior to that of placebo, in double-blind comparison using placebo as a control (see Narabayashi et al., "clinical evaluation" vol. 15 (No. 3) 423-457(1987): Clin. Eval., 15: 423-457, 1987, October). However, the efficacy rate of DOPS was not necessarily high. In the Societas Neurologica Japonica PA disease guideline, therefore, DOPS is regarded as a medicament to be optionally tried, and its effectiveness was questioned outside Japan.

The reason for the limited effect of DOPS is considered to be attributable to low conversion efficiency of DOPS as an amine precursor to NE as compared to L-DOPA. That is, as compared to L-DOPA, the decarboxylation reaction rate of DOPS is low, and transferability of DOPS into the brain is low, based on which facts, a negative report has been documented that DOPS cannot be expected as an intracerebral NE precursor amino acid (see G. Bartholini et al., J. Pharmacology & Experimental Therapeutics, 193, 523-532(1975)).

In view of the foregoing, the development of a therapeutic agent and a treatment method for the improvement and treatment of axial symptoms (particularly, freezing of gait) of patients with PA disease, for which L-DOPA therapy is ineffective, has been desired.

SUMMARY OF THE INVENTION

The problem of the present invention is to provide a therapeutic agent for treating axial symptoms (i.e., gait disturbance, abnormal postural sway, and, particularly, freezing of gait) of patients with Parkinson's disease, for which various DA nerve activators such as L-DOPA preparation and the like are ineffective, which contains DOPS and a COMT inhibitor. A "DA nerve activator" is understood to refer to a compound that increases DA levels in the central nervous system (CNS) or a compound that stimulates DA receptors independent of DA levels.

The present disclosure arises from long-time work including treatment of patients with PA disease, and the disclosure incorporates various studies by the inventors with particular focus placed on the improvement and treatment of axial symptoms (particularly, freezing of gait), for which L-DOPA preparation is ineffective. First, the present inventors have newly prepared a freezing of gait VAS (visual analogue scale) as an evaluation measure to clarify pathological changes for an accurate evaluation of a treatment effect on axial symptoms (particularly, freezing of gait) of patients with PA disease, and made an evaluation based thereon.

As a result, it was found that the axial symptoms (particularly, freezing of gait) of patients with PA disease can be remarkably improved by newly adding a COMT inhibitor and using the same in combination with an L-DOPA preparation, rather than using DOPS singly. It has also been observed that a combined use of only DOPS and a COMT inhibitor is effective even when an L-DOPA preparation is not used in combination.

As a result of the above, the present inventors have found that a combined administration of DOPS and a COMT inhibitor enables effective improvement and treatment of the axial symptoms (particularly, freezing of gait) of patients with PA disease. The present disclosure is based on these findings.

The present invention, in various embodiments, encompasses the following.

(1) A therapeutic agent for treating an axial symptom of a patient with PA disease, which is the combination of DOPS and a COMT inhibitor (in the same or separate formulations), or a combined use of DOPS and a COMT inhibitor.

(2) The therapeutic agent of the above-mentioned (1), wherein the combination further includes a DA nerve activator (all three in the same formulation, two of the three in the same formulation, or all three in separate formulations), or the combined use further includes a DA nerve activator.

(3) The therapeutic agent of the above-mentioned (1) or (2), wherein the DA nerve activator is an L-DOPA preparation.

(4) The therapeutic agent of any of the above-mentioned (1) to (3), wherein the patient with PA disease shows a symptom of a moderate level or higher.

(5) The therapeutic agent of any of the above-mentioned (1) to (4), wherein the patient with PA disease falls under at least one of the following items:
a) a Parkinsonian patient with Hoehn & Yahr scale (hereinafter H&Y) grade III or above and freezing of gait symptom, who is diagnosed by a doctor in charge to be "freezing often" or "freezing always" in the off state according to a freezing of gait evaluation scale (VAS),
b) a patient with PA disease who is administered with not less than 200 mg/day of L-DOPA in 3-6 portions per day.

(6) The therapeutic agent of any of the above-mentioned (1) to (5), wherein the PA patient falls under all of the above-mentioned items a) and b).

(7) The therapeutic agent of the above-mentioned (1), wherein the PA patient does not respond to an L-DOPA preparation.

(8) The therapeutic agent of any of the above-mentioned (1) to (7), wherein the COMT inhibitor is entacapone, tolcapone, or nitecapone.

(9) The therapeutic agent of any of the above-mentioned (1) to (8), which is a combined use of an L-DOPA preparation, DOPS and entacapone.

(10) The therapeutic agent of any of the above-mentioned (1) to (9), wherein the combined use is simultaneous administration.

(11) The therapeutic agent of any of the above-mentioned (1) to (10), wherein the dose of DOPS is 300-1200 mg/day.

(12) The therapeutic agent of any of the above-mentioned (1) to (10), wherein the dose of DOPS is 300-900 mg/day.

(13) The therapeutic agent of any of the above-mentioned (1) to (10), wherein the dose of the COMT inhibitor is 150-1200 mg/day.

(14) The therapeutic agent of any of the above-mentioned (1) to (10), wherein the dose of COMT inhibitor is 150-600 mg/day.

(15) The therapeutic agent of any of the above-mentioned (1) to (14), wherein the DOPS and entacapone are each used at 100 mg/dose in combination with the L-DOPA preparation.

(16) The therapeutic agent of any of the above-mentioned (1) to (15), wherein the axial symptom is freezing of gait.

(17) A method of treating an axial symptom of Parkinson's disease in a patient suffering from the disease, comprising administering L-threo-3,4-dihydroxy-phenylserine and a COMT inhibitor.

(18) The method of the above-mentioned (17), comprising further administering a DA nerve activator in combination.

(19) The method of the above-mentioned (18), wherein the DA nerve activator is an L-DOPA preparation.

(20) The method of any of the above-mentioned (17) to (19), wherein the axial symptom is freezing of gait.

(21) A method of treating an axial symptom of Parkinson's disease in a patient suffering from the disease, comprising administering DOPS and a COMT inhibitor and also using a freezing of gait evaluation scale (VAS) as an index of the treatment.

(22) The method of the above-mentioned (21), further comprising use of a DA nerve activator.

(23) The combination of L-threo-3,4-dihydroxy-phenylserine, or a pharmaceutically acceptable ester, amide, salt, solvate, or prodrug thereof, and a COMT inhibitor (in the same or separate formulations) for use in treating an axial symptom of Parkinson's disease in a patient exhibiting the axial symptom of the disease.

(24) The combination according to the above-mentioned (23), wherein the COMT inhibitor is selected from the group consisting of entacapone, tolcapone, and nitecapone.

(25) The combination according to the above-mentioned (23) or (24), further comprising a dopamine nerve activator (all three in the same formulation, two of the three in the same formulation, or all three in separate formulations).

(26) The combination according to any of the above-mentioned (23)-(25), wherein the dopamine nerve activator comprises L-DOPA.

(27) The combination according to any of the above-mentioned (23)-(26), wherein the patient exhibits the axial symptom of the disease at a moderate level or higher as indicated by a Hoehn & Yahr scale score of not less than Ill or daily living ability grade of not less than II.

(28) The combination according to any of the above-mentioned (23)-(27) wherein the axial symptom exhibited by the patient is selected from the group consisting of gait disturbance, abnormal postural sway, and, freezing of gait.

(29) The combination according to any of the above-mentioned (23)-(28), wherein the patient exhibits a Hoehn & Yahr scale score of III or above, exhibits the axial symptom of freezing of gait, and is diagnosed to be "freezing often" or "freezing always" in the off state as evaluated according to a freezing of gait evaluation scale.

(30) The combination according to any of the above-mentioned (23)-(29), wherein the patient has previously been diagnosed as being non-responsive to L-DOPA therapy.

(31) The combination according to any of the above-mentioned (23)-(30), wherein the combination comprises an L-DOPA preparation, L-threo-3,4-dihydroxy-phenylserine, or a pharmaceutically acceptable ester, amide, salt, solvate, or prodrug thereof, and entacapone.

(32) Use of L-threo-3,4-dihydroxy-phenylserine, or a pharmaceutically acceptable ester, amide, salt, solvate, or prodrug thereof, and a COMT inhibitor in the preparation of a medicament for treating an axial symptom of Parkinson's disease in a patient exhibiting the axial symptom of the disease.

As further disclosed herein, the therapeutic agent of the present invention is highly effective as a therapeutic agent for axial symptoms of patients with PA disease (particularly patients with PA disease who are not responsive to an L-DOPA preparation), for which an effective treatment method has not been found. That is, a clinical study using a freezing of gait evaluation scale (VAS) has shown that the therapeutic agent of the present invention is effective for treating the axial symptoms of PA disease (particularly freezing of gait) and, as a result, the therapeutic agent of the present invention is considered to have high possibility of becoming the standard of a method for treating patients exhibiting the axial symptoms of PA disease. From the foregoing, the treatment method of the present invention is considered to have a high priority in terms of usefulness in the treatment strategy of PA syndrome.

BRIEF DESCRIPTION OF THE DRAWING

FIG. 1 shows the freezing of gait evaluation scale (VAS) in the present invention. Pathologic evaluation of patients with PA disease by using this scale has enabled more appropriate pharmacological evaluations.

DETAILED DESCRIPTION

In the present invention, "DOPS" refers to L-threo-3,4-dihydroxy-phenylserine, also referred to as L-threo-DOPS, and encompasses pharmaceutically acceptable esters, amides, salts, solvates, or prodrugs of DOPS. DOPS in the present invention is characteristically administered simultaneously with the below-mentioned COMT inhibitor, and the dose is, for example, 300-1200 mg/day, preferably 300-900 mg/day, more preferably 300-600 mg/day. DOPS in the present invention can be administered in 3-6 portions per day according to the symptom. DOPS may be administered as a sustained-release composition (e.g., once daily or twice daily). DOPS also may be administered as an immediate-release composition (e.g., once daily, twice daily, three times daily, four times daily, five times, daily, or six times daily). DOPS may be administered in a combined sustained-release and immediate-release form.

In the present invention, the "DA nerve activator" refers to a medicament that activates DA receptors or increases dopamine levels in the central nerve system. Effective DA never activators that can be used according to the present invention include, for example, L-DOPA (Dopaston®), L-DOPA/carbidopa combination agent (Neodopaston®, Menesit®), L-DOPA/benserazide combination agent (Madopa®), cabergoline (Cabaser®), bromocriptine (Parlodel®), amantadine (Symmetrel®) and the like. Preferred DA nerve activators are L-DOPA preparations such as L-DOPA (Dopaston®), L-DOPA/carbidopa combination agent (Neodopaston®), and the like.

In the present invention, the "L-DOPA preparation" is not particularly limited as long as it is a known preparation containing L-DOPA. For example, L-DOPA and carbidopa preparation, and L-DOPA and benserazide hydrochloride preparation can be mentioned.

In the present invention, the "catechol-O-methyl group transferase (COMT) inhibitor" refers to an agent that suppresses the activity of COMT which is an enzyme capable of methylating the 3-position hydroxyl group of the catechol ring. Since COMT is well known to catabolize L-DOPA and DA, a COMT inhibitor is currently used to maintain persistence of L-DOPA outside the brain and augment DA activity in the brain.

COMT inhibitors already used for such L-DOPA therapy, and medicaments generally acknowledged as COMT inhibitors can be similarly used in the present invention. Representative examples of the COMT inhibitor to be used in combination with DOPS in the present invention include entacapone (Comtan®), tolcapone (Tasmar®), nitecapone, and the like.

In the present invention, a COMT inhibitor is administered in combination with DOPS. The dose thereof is, for example, 150-1200 mg/day, preferably 150-600 mg/day, more preferably 150-300 mg/day. Like DOPS in the present invention, it can be administered in 3-6 portions per day according to the symptom.

There are reports on the effectiveness of a combination agent of DOPS and a COMT inhibitor when administered to rat animal model of mood disorder, sleep disorder or attention deficit disorder, rat animal model of neurally mediated hypotension, and rat animal model of fibromyalgia syndrome (see U.S. Pub. No. 2008/0221170, U.S. Pub. No. 2008/0227830, and U.S. Pub. No. 2009/0023705, the disclosures of which are incorporated herein by reference in their entireties). However, there is no known disclosure relating to the treatment of freezing of gait of PA patients, nor is there any description relating to appropriate doses of DOPS and a COMT inhibitor for the treatment of freezing of gait.

In the present invention, the term "patients with Parkinson's (PA) disease" means patients affected with Parkinson's disease. According to the Merck Manual (18$^{th}$ Edition), Parkinson's disease is described to be an idiopathic, slowly progressive, degenerative CNS disorder characterized by such symptoms as bradykinesia, akinesia, muscular rigidity, resting tremor, and postural instability. In Parkinson's disease, pigmented neurons of the substantia nigra, locus ceruleus, and other brain stem dopaminergic cell groups disappear. Loss of substantial nigra neurons, which project into the caudate nucleus and putamen, depletes DA in these areas. The cause is unknown.

The symptoms commonly observed in Parkinson's disease are bradykinesia (movement takes time), muscular rigidity (muscle becomes stiff), and tremor (shaking). All these symptoms do not always emerge and, in some cases, only tremor manifests, or only movement becomes slow. Since the movement becomes slow, for example, Parkinson's disease patients show symptoms of difficulty in turning in bed, longer time required for getting out of bed and the like; however, motor paralysis and weakness of limbs are not normally seen. Since the muscle becomes stiff and movement becomes less, the patients more often tend to sit still with a round back. As for shaking, the symptom of tremor of one hand or leg when at rest is typically seen, but the level varies from patients without tremor to those with persistent tremor of both hands. Tremor is one of the symptoms the patients are most concerned about, but the level of tremor is generally considered not much related to the severity of the disease.

These symptoms are said to be three major symptoms, and as the symptoms progress, the patients tend to fall down easily. This is considered to be because disruption of body balance leads to disorder of balancing mechanism which keeps the body from falling down (postural reflex) (postural reflex disorder).

Postural instability develops, resulting in gait abnormalities. Patients have difficulty in starting to walk, turning, and stopping; the gait becomes shuffling with short steps, and the arms are held flexed to the waist, and do not swing with the stride. Steps may inadequately quicken, and patients may break into a run to keep from falling (festination). A tendency to fall forward (propulsion) or backward (retropulsion) are seen, when the center of gravity is displaced resulting from loss of postural refluxes.

In the present invention, the "axial symptoms" refers to, of the aforementioned symptoms of Parkinson's disease, decrease of body axis rotation and axial dysfunction. That is, it refers to the symptoms of disorder of movements such as turning in bed movement and getting up movement on the bed, change of direction during walking, and the like.

In the present invention, the "symptom of a moderate level or higher" refers to patients showing freezing of gait and postural maintenance disorder, for example, patients with symptoms of a moderate or severe level such as having a H&Y severity classification grade of not less than III and/or daily living ability grade of not less than II.

In the present invention, the "freezing of gait evaluation scale (VAS)" refers to a subjective evaluation method of freezing of gait according to Visual Analog Scale (VAS), and evaluation according to the scale shown in FIG. 1 and the evaluation method described in Example 4. Conventionally, VAS is often used for the evaluation of subjective sensation of subjects such as "pain" and "fatigue", and its reliability and validity have been confirmed by Rigakuryoho Kagaku, 21(1): 31-35, (2006).

On the other hand, as a unified evaluation method for comprehensive evaluation of the symptoms of Parkinson's disease, the Unified Parkinson's Disease Rating Scale (UPDRS) was formed in 1987 and is widely used all over the world mainly for evaluation in clinical trials since it enables detailed evaluation as compared to H&Y classification. The symptom of freezing of gait is generally evaluated using UPDRS. However, it includes too many evaluation items for the evaluation of efficacy relating to the improvement of freezing of gait to the extent an appropriate evaluation of freezing of gait is difficult. Use of VAS has enabled an appropriate evaluation of Quality Of Life (QOL) relating to freezing of gait. As a result, the effect of a medicament for freezing of gait can now be appropriately evaluated. Beneficially, treatment according to the invention can improve VAS score by at least 15%, at least 20%, at least 25%, at least 30%, or at least 40%.

The active agent compounds described herein can be administered in the raw chemical form or as one or more pharmaceutical compositions. Such compositions can comprise the pharmaceutically active compounds, or pharmaceutically acceptable esters, amides, salts, solvates, analogs, derivatives, or prodrugs thereof. The composition can comprise a single composition containing all of the active agents. Alternately, the composition can comprise multiple compositions comprising separate active agents but intended to be administered simultaneously, in succession, or in another defined period of proximity. The active agent compounds can be combined with one or more pharmaceutically acceptable carriers therefore, and optionally, other therapeutic agents or excipients. Carriers should be acceptable in that they are compatible with any other agents of the composition and not harmful to the recipient thereof. A carrier may also reduce any undesirable side effects of the agent. Such carriers are known in the art. See, Wang et al. (1980) J. Parent. Drug Assn. 34(6):452-462, herein incorporated by reference in its entirety. Compositions may include short-term, rapid-onset, rapid-offset, controlled release, sustained release, delayed release, and pulsatile release compositions, providing the compositions achieve administration of a compound as described herein. See *Remington's Pharmaceutical Sciences* ($18^{th}$ ed.; Mack Publishing Company, Eaton, Pa., 1990), herein incorporated by reference in its entirety. The compositions can be for any of oral, parenteral (including intravenous, intramuscular, subcutaneous, intradermal, intra-articular, intra-synovial, intrathecal, intra-arterial, intracardiac, subcutaneous, intraorbital, intracapsular, intraspinal, intrasternal, and transdermal), topical (including dermal, buccal, and sublingual), vaginal, urethral, and rectal administration. Administration can also be via nasal spray, surgical implant, internal surgical paint, infusion pump, or via catheter, stent, balloon or other delivery device. The compositions can be prepared by combining (by various methods) the active compounds of the invention with a suitable carrier or other adjuvant, which may consist of one or more ingredients. The combination of the active agents with the one or more adjuvants is then physically treated to present the composition in a suitable form for delivery (e.g., shaping into a tablet or forming an aqueous suspension), such as tablets, capsules, caplets, and wafers (including rapidly dissolving or effervescing), each containing a predetermined amount of the active agent. The compositions may also be in the form of a powder or granules, a solution or suspension in an aqueous or non-aqueous liquid, and as a liquid emulsion (oil-in-water and water-in-oil). The active agents may also be delivered as a bolus, electuary, or paste. It is generally understood that methods of preparations of the above dosage forms are generally known in the art, and any such method would be suitable for the preparation of the respective dosage forms for use in delivery of the compositions according to the present invention.

EXAMPLES

The present invention is explained in more detail in the following by referring to Examples and experimental example, which are not to be construed as limiting.

Example 1

Treatment effect of therapeutic agent of the present invention for PA disease patient with wearing-off phenomenon
(1) Treatment Target Patients
A PA patient with severity of H&Y grade III (showing wearing-off phenomenon and freezing of gait in ON state): 56-year-old female (disease duration 19 years).
(2) Clinical Tests and Results
An L-DOPA preparation (Menesit, 400 mg/day) was administered in 7 portions, a dopamine agonist (Permax®, 750 μg/day) was administered in 3 portions, a selective MAO-B inhibitor (FP, 5 mg/day) was administered in 2 portions, and an anticholinergic drug (Artane, 3 mg/day) was administered in 3 portions. However, the wearing-off phenomenon and freezing of gait in the ON state were observed. Falling down occurred once a month.
When the L-DOPA preparation (Menesit, 700 mg/day) was administered in 7 portions, DOPS (700 mg/day) and a COMT inhibitor (Comtan®, 700 mg/day) were simultaneously administered in 7 portions each. Freezing of gait mostly disappeared from immediately after administration. In addition, falling down did not occur.
(3) Evaluation
In a PA patient showing wearing-off phenomenon and freezing of gait in the ON state due to long-term ingestion of an L-DOPA preparation (Menesit) and the like, the axial symptoms could be markedly improved by simultaneous administration of DOPS and Comtan® together with the L-DOPA preparation (Menesit).

Example 2

Treatment effect of therapeutic agent of the present invention for PA disease patient with pure akinesia and chief complaint of freezing of gait
(1) Treatment Target Patient
A PA disease patient with pure akinesia and chief complaint of freezing of gait: 66-year-old female.
(2) Clinical Tests and Results
a) DOPS (300 mg/day) was administered in 3 portions, but ineffective.
b) DOPS (300 mg/day) and Comtan® (300 mg/day) as a COMT inhibitor were simultaneously administered in 3 portions each. As a result, a mild improvement was observed.
c) DOPS (600 mg/day) and Comtan® (300 mg/day) as a COMT inhibitor were simultaneously administered in 3 portions each. As a result, freezing of gait on U-turn disappeared.
(3) Evaluation
Combined use of DOPS and Comtan® (COMT inhibitor) was effective even in a treatment without using an L-DOPA preparation and a dopamine receptor stimulator.

Example 3

Treatment effect of therapeutic agent of the present invention for PA disease patient with pure akinesia and chief complaint of freezing of gait (patient not responsive to L-DOPA preparation)
(1) Treatment Target Patient
A PA disease patient with pure akinesia and chief complaint of freezing of gait, not responsive to L-DOPA preparation: 69-year-old male.
(2) Clinical Tests and Results
a) DOPS (600 mg/day) was administered in 3 portions, and a slight improvement effect was observed.
b) DOPS (600 mg/day) and Comtan® (300 mg/day) as a COMT inhibitor were administered in combination in 3 portions, and the effect expanded to enable him to go out with a handcart.
(3) Evaluation
A combined use of DOPS and a COMT inhibitor was effective for the "freezing of gait symptom" for which L-DOPA preparation is not effective.

Example 4

Treatment effect of therapeutic agent of the present invention for PA disease patient with freezing of gait symptom
To verify superior effect of the therapeutic agent of the present invention comprising DOPS and a COMT inhibitor for "freezing of gait" as compared to DOPS alone and COMT inhibitor alone, a 3 group-comparison test by random allocation was performed as follows.
(1) Treatment Target Patients (Selection Criteria)
Patients who satisfied all following conditions when the observation was started were the target subjects.
a) A consent to participate in the test has been obtained from the participant him/herself by virtue of explanation document and written consent.
b) The age when the consent was obtained is 20 years old or older and less than 80 years old, gender unquestioned.
c) A PA disease patient on H&Y grade III or above and having a freezing of gait symptom diagnosed by the doctor in charge to be "freezing often" or "freezing always" in the OFF state according to the freezing of gait evaluation scale of FIG. 1.
d) A patient under L-DOPA/carbidopa or L-DOPA/benserazide hydrochloride administration and suffering from diurnal variation (wearing-off phenomenon).
e) A patient under administration of not less than 300 mg/day of L-DOPA in not less than 3 portions and not more than 6 portions.
(2) Clinical Test Design
The following interventional test (0-4 week) was performed. The patients were divided for randomized, unblinded, and 3-group-comparison tests and, as described in the following section, group A was a DOPS/entacapone combined administration group, group B was an entacapone single administration group, and group C was a DOPS single administration group. Two weeks from the start of the administration was taken as a titration period, and the symptoms were evaluated at 4 weeks from the start of the administration.
a) Titration period (2 weeks): Group 1—DOPS singly; Group 2—entacapone singly; Group 3—combined use of entacapone and DOPS.
On day one, entacapone and(or) DOPS are(is) administered in an amount of 100 mg each simultaneously with L-DOPA/DCI preparation first thing in the morning.
Two days later, entacapone and(or) DOPS are(is) administered in an amount of 100 mg each simultaneously with L-DOPA/DCI preparation first or second thing in the morning.
Thereafter, the administration frequency of entacapone and(or) DOPS (100 mg each) is each increased by one every other day. They are always administered simultaneously with the administration of L-DOPA/DCI preparation, and the administration frequency is sequentially added to an earlier administration time of L-DOPA/DCI preparation.

In all groups, entacapone and(or) DOPS are(is) administered in an amount of 100 mg each simultaneously with the administration of L-DOPA/DCI preparation (maximum 6 times).

b) Maintenance period (4 weeks):

Entacapone and(or) DOPS are(is) administered in an amount of 100 mg each simultaneously with the administration of L-DOPA/DCI preparation (maximum 6 times).

The dosage and dose regimen of antiparkinsonian drugs including L-DOPA/DCI preparation are not changed for 0-4 weeks.

(3) Allocation Method

A test director (contributory) doctor confirms that test subjects meet the selection criteria and does not fall within the exclusion criteria. Thereafter, necessary items are described in "case registration form", medical record numbers are replaced to optional patient IDs, and the documents are sent to Osaka University Graduate School of Medicine Neurology laboratory. In this case, a treatment group allocated for the patients is determined based on random number codes generated by a computer according to a block sorting method.

(4) Evaluation Method

The evaluation is made by a contributory doctor other than the doctor in charge, who has no knowledge of the allocation.

Evaluation item: freezing of gait VAS (visual analogue scale).

A line is drawn from the state of zero freezing of gait to the state of 100 thereof, the current state of freezing of gait is indicated on the line, and the freezing of gait is quantified by the distance from zero (an increase in value indicating a worsening of the freezing of gait).

(5) Results

The evaluation considered seven cases in Group A, five cases in group B, and five cases in group C. The evaluation results of the effect according to the freezing of gait VAS scale before and after the treatments described above are shown in Table 1.

TABLE 1

| Group | Individual | Score Pre-Treatment | Score Post-Treatment |
|---|---|---|---|
| 1 | 1 | 69 | 37 |
|   | 2 | 54 | 62 |
|   | 3 | 72 | 94 |
|   | 4 | 60 | 58 |
|   | 5 | 62 | 20 |
| 2 | 1 | 23 | 24 |
|   | 2 | 34 | 50 |
|   | 3 | 56 | 56 |
|   | 4 | 49 | 15 |
|   | 5 | 83 | 83 |
| 3 | 1 | 65 | 41 |
|   | 2 | 44 | 20 |
|   | 3 | 76 | 8 |
|   | 4 | 78 | 66 |
|   | 5 | 81 | 78 |
|   | 6 | 19 | 24 |
|   | 7 | 38 | 29 |

Based on the above-mentioned results of Table 1, statistical analysis was performed using the mean pre- and post-treatment scores for each group and the Paired Student-t-test. As a result, an improvement effect (significant difference) on freezing of gait between before and after administration was observed only in Group 3. This is shown below in Table 2.

TABLE 2

| Group | n | Mean Score Pre-Treatment | Mean Score Post-Treatment | t |
|---|---|---|---|---|
| 1 | 5 | 63.4 | 54.2 | 0.2443 |
| 2 | 5 | 49 | 45.6 | 0.3504 |
| 3 | 7 | 57.3 | 38 | 0.0384 |

The symptoms of Parkinson's disease are classified with symptoms of four limbs (tremor and muscle rigidity) and axial symptoms (freezing of gait, gait difficulty, abnormal posture etc.). It has been found that L-DOPA preparations are effective for the former symptoms. However, no effective treatment method has been found for the latter symptoms. As shown in the above-mentioned Table 2, a combined use of an L-DOPA preparation, DOPS and entacapone has been proved effective for the improvement of axial symptoms of Parkinson's disease (particularly freezing of gait).

Using the therapeutic agent of the present invention, effective results could be obtained for the freezing of gait symptom of PA patients of a moderate level or higher, for whom L-DOPA therapy fails to show improvements. That is, the effectiveness of the treatment method of the present invention, including use of DOPS and a COMT inhibitor, such as entacapone, in combination and the freezing of gait VAS scale, for the freezing of gait symptom of Parkinson's disease has been shown. As a result, the therapeutic agent of the present invention can enhance QOL of patients with progressive symptoms of Parkinson's disease, and can provide a more effective therapeutic agent for patients not responsive to the conventional L-DOPA therapy. Furthermore, the therapeutic agent of the present invention has high possibility of becoming a basic therapeutic agent for the axial symptoms of Parkinson's disease and is highly useful as a treatment method for Parkinson's syndrome.

The invention claimed is:

1. A method for treating an axial symptom of Parkinson's disease comprising administering a combination of L-threo-3,4-dihydroxy-phenylserine and a COMT inhibitor to a patient exhibiting the axial symptom of the disease.

2. The method according to claim 1, wherein the COMT inhibitor is selected from the group consisting of entacapone and tolcapone.

3. The method according to claim 2, wherein the COMT inhibitor is entacapone.

4. The method according to claim 1, wherein the L-threo-3,4-dihydroxy-phenylserine and the COMT inhibitor are administered in the same formulation.

5. The method according to claim 1, wherein the L-threo-3,4-dihydroxy-phenylserine and the COMT inhibitor are administered in separate formulations.

6. The method according to claim 1, wherein the combination further includes a dopamine nerve activator.

7. The method according to claim 6, wherein the dopamine nerve activator comprises L-DOPA.

8. The method according to claim 6, wherein the L-threo-3,4-dihydroxy-phenylserine the COMT inhibitor, and the dopamine nerve activator are administered in the same formulation.

9. The method according to claim 6, wherein the L-threo-3,4-dihydroxy-phenylserine the COMT inhibitor, and the dopamine nerve activator are administered in two or three separate formulations.

10. The method according to claim 1, wherein the patient exhibits the axial symptom of the disease at a moderate level or higher as indicated by a Hoehn & Yahr scale score of not less than III or daily living ability grade of not less than II.

11. The method according to claim 1, wherein the axial symptom exhibited by the patient is selected from the group consisting of gait disturbance, abnormal postural sway, and freezing of gait.

12. The method according to claim 11, wherein the axial symptom exhibited by the patient is freezing of gait.

13. The method according to claim 1, wherein the patient exhibits a Hoehn & Yahr scale score of III or above, exhibits the axial symptom of freezing of gait, and is diagnosed to be "freezing often" or "freezing always" in the off state as evaluated according to a freezing of gait evaluation scale.

14. The method according to claim 1, wherein the patient has previously been diagnosed as being non-responsive to L-DOPA therapy.

15. The method according to claim 1, comprising administering an L-DOPA preparation, L-threo-3,4-dihydroxy-phenylserine and entacapone.

16. The method according to claim 1, wherein the L-threo-3,4-dihydroxy-phenylserine is administered in a sustained-release form.

17. The method according to clam 1, wherein the L-threo-3,4-dihydroxy-phenylserine is administered in an immediate-release form.

18. The method according to claim 17, wherein the combination is administered in two or more daily doses.

* * * * *